United States Patent
Conradsen (10) Patent No.: US 10,420,499 B2
(45) Date of Patent: Sep. 24, 2019

(54) METHOD AND SYSTEM OF DETECTING SEIZURES

(71) Applicant: Brain Sentinel, Inc., San Antonio, TX (US)

(72) Inventor: Isa Conradsen, København S (DK)

(73) Assignee: Brain Sentinel, Inc., San Antonio, TX (US)

(*) Notice: Subject to any disclaimer, the term of this patent is extended or adjusted under 35 U.S.C. 154(b) by 1088 days.

(21) Appl. No.: 14/407,249

(22) PCT Filed: Jun. 11, 2013

(86) PCT No.: PCT/DK2013/050189
§ 371 (c)(1),
(2) Date: Dec. 11, 2014

(87) PCT Pub. No.: WO2013/185775
PCT Pub. Date: Dec. 19, 2013

(65) Prior Publication Data
US 2015/0119746 A1    Apr. 30, 2015

(30) Foreign Application Priority Data

Jun. 12, 2012 (DK) .................... 2012 70323

(51) Int. Cl.
| | | |
|---|---|---|
| *A61B 5/00* | (2006.01) | |
| *A61B 5/0488* | (2006.01) | |
| *A61B 5/04* | (2006.01) | |

(52) U.S. Cl.
CPC ........ *A61B 5/4094* (2013.01); *A61B 5/04014* (2013.01); *A61B 5/0488* (2013.01); *A61B 5/7246* (2013.01)

(58) Field of Classification Search
CPC .................................................. A61B 5/4094
See application file for complete search history.

(56) References Cited

U.S. PATENT DOCUMENTS

| 6,097,980 A | 8/2000 | Monastra et al. |
|---|---|---|
| 6,543,448 B1 | 4/2003 | Smith et al. |

(Continued)

FOREIGN PATENT DOCUMENTS

| WO | 02/49500 A2 | 6/2002 |
|---|---|---|
| WO | 02/064024 A2 | 8/2002 |

(Continued)

OTHER PUBLICATIONS

Jerome Engel, Jr. and Timothy A. Pedley, Generalized Tonic-Clonic Seizures, Epilepsy a Comprehensive Textbook, Second Edition, vol. One, Lippincott Williams & Wilkins, pp. 553-562.

(Continued)

*Primary Examiner* — Daniel L Cerioni
*Assistant Examiner* — Yasmeen S Warsi
(74) *Attorney, Agent, or Firm* — Pizarro Allen PC (57) ABSTRACT

A system and method for detecting and analyzing the characteristics of seizures, such as tonic-clonic seizures, comprising at least one processor unit capable of recording a signal from a sensor unit, one or more analysis modules configured to analyze the recorded signal, one or more evaluation modules configured to evaluate the output signals from the analysis modules. A first analysis module is configured to analyze the recorded signal within a first frequency band, and a second analysis module is configured to analyze the recorded signal within a second frequency band, and the evaluation module is configured to calculate the ratio between the two output signals from the analysis modules. The system includes a seizure detection module configured to detect a seizure and a time-point extraction module configured to determine at least one starting point and an end point of the seizure.

10 Claims, 4 Drawing Sheets

(56) References Cited

U.S. PATENT DOCUMENTS

| | | |
|---|---|---|
| 8,738,136 B2 | 5/2014 | Frei et al. |
| 2013/0183229 A1 | 7/2013 | Garcia-Martinez |

FOREIGN PATENT DOCUMENTS

| | | |
|---|---|---|
| WO | 2008/131782 A1 | 11/2008 |
| WO | 2012/051628 A1 | 4/2012 |

OTHER PUBLICATIONS

ISA Conradsen, Peter Wolf, Thomas Sams, Helge B.D. Sorensen, and Sándor Beniczky, Patterns of Muscle Activation During Generalized Tonic and Tonic-Clonic Epileptic Seizures, Epilepsia, 52(11), Wiley Periodicals,Inc., pp. 2125-2132.

METHOD AND SYSTEM OF DETECTING SEIZURES

BACKGROUND OF THE INVENTION

Field of the Invention

The present invention relates to a system for detecting seizures, such as tonic-clonic seizures, comprising:
- at least one processor unit capable of recording an electromyographic signal from a sensor unit,
- one or more analysis modules configured to analyze the recorded signal, and
- one or more evaluation modules configured to evaluate the output signals from the analysis modules.

The present invention further relates to a method of analyzing the dynamics of a seizure, such as tonic-clonic seizures, comprising the steps:
- recording an electromyographic signal from a sensor unit,
- analyzing the recorded signal using one or more analysis modules, and
- evaluating the output signal using one or more evaluation modules.

Description of Related Art

It is well known to analyze abnormal biomedical events, such as seizures, in order to determine the characteriztics of the seizure which may then be used to detect or identify another seizure or other similar seizures. This method is particular relevant when detecting or predicting the onset of seizures.

Today, people suffering from seizures occurring from abnormal neuronal activities, such as epileptic seizures, need to be admitted to special clinics or hospitals where the medical staffs, such as primary caregivers, doctors or neurologists, are able to analyze, manage and classify the seizures. Once admitted, seizures are often detected and recorded by using multiple signal processing means, e.g., video-EEG, CT- and MRI-scanning, EEG and CT/MRI-scanning, motion detection or other signal processing means. This process is not only very time consuming, but also requires a lot of data analysis either automatically or manually in order to determine the characteriztics of the seizure.

Generalized tonic-clonic seizures (also called GTCS or GTC seizures) are the most common afebrile seizure type in the general population and also the most dramatic of all seizures. However, the underlying pathophysiologic mechanisms (dynamics) are not yet fully elucidated since it is obscured by artifacts. Most of the data come from in-vitro studies or animal models (see, Zifkin, B. G., Dravet, C. (2008) *Generalized tonic-clonic seizures*. In J. Engel, Jr, T. A. Pedley (Eds) Epilepsy. A comprehensive textbook. 2nd ed., Lippincott, Williams a Wilkins, Philadelphia, vol 1, pp. 553-562). The in-vivo human data on the electrophysiology of the GTCS are mainly based on EEG recordings in the 1950ies from patients who were curarized (to avoid artifacts) and had GTCS induced by administration of pro-convulsive drugs such as pentetrazol or bemegride (see, Ajmone-Marsan, C. and Ralston, B. L. *The Epileptic Seizure. Its Functional Morphology and Diagnostic Significance*, Charles C Thomas, Springfield, Ill.; 1957 (pp. 65-72), and Gastaut, H. and Broughton, R. *Clinical and electroencephalographic features, diagnosis and treatment*, Epileptic Seizures. Charles C. Thomas, Springfield, Ill.; 1972 (pp. 26-47)).

GTC seizures are commonly divided into a tonic phase and a clonic phase and the whole seizure period often lasts no more than a few minutes. Muscles are at the end of the common final neural pathway involved in the GTCS, and surface electromyography (sEMG) signals provide valuable information at a high temporal resolution. A previous study (see Conradsen et al., *Patterns of muscle activation during generalized tonic and tonic-clonic epileptic seizures*, Epilepsia, Volume 52, Issue 11, 2011) has shown that the quantitative sEMG parameters calculated for the whole seizure period differed significantly among a GTCS, a tonic seizure and a voluntary activation acted by healthy controls.

Today, the start-points and stop-points of the seizure period and of the different phases occurring in the seizure period are often determined manually by the person(s) analyzing the signals. This leads to some uncertainty about the precise start- and stop-point for each phase and the length (period) of the seizure.

SUMMARY OF THE INVENTION

It is an object of the invention to provide a system and method capable of analyzing the dynamics of tonic-clonic seizures.

It is an object of the invention to provide a system and method capable of determining the length of the whole seizure period.

It is an object of the invention to provide a system and method capable of detecting the start point and the end point of the seizure. It is another object of the invention to provide a system and method capable of detecting GTC seizures.

As mentioned above, the invention relates to a system for detecting seizures, such as tonic-clonic seizures, characterized in that:
- a first analysis module is configured to analyze the recorded signal within a first frequency band of 32-512 Hz, and a second analysis module is configured to analyze the recorded signal within a second frequency band of 2-16 Hz, and
- the evaluation module is configured to calculate the ratio between the first output signal and the second output signal.

This enables the characteriztics and thereby the dynamics of the seizure to be determined automatically without requiring a visual inspection each time, since studies have shown that the power characteriztics of the tonic phase and the clonic phase are mainly located in two different frequency bands: a low frequency band and a high frequency band. The power generated in the tonic phase and in the clonic phase may then be extracted using different frequency bands, thus allowing the dynamics of each phase to be analyzed separately or in relation to each other. The ratio between the power of the low and high frequency bands of the electromyographic signal provides the best way to determine the dynamics of the seizure. Thereby, providing a system capable of analyzing the dynamics of a seizure after a seizure has occurred, but also detecting a seizure.

According to a specific embodiment of the invention, a seizure detection module is configured to compare the ratio to a first threshold value and to generate an event signal if the ratio exceeds the first threshold value. According to a further specific embodiment, the seizure detection module is configured to further compare one of the output signals to a second threshold value and to generate the event signal if the output signal exceeds the second threshold value.

This enables the system to detect a seizure, in particular a tonic-clonic seizure, by simply analyzing the power ratio within the two frequency bands. The number of false positives may be further reduced by also checking that the power of the high frequency is above a certain level since this type of seizures is known to have a high amount of power in this frequency band. This reduces the need for measuring multiple signals in order to detect a seizure with a low false positive detection rate.

According to one embodiment of the invention, a time-point extraction module is configured to compare one of the output signals to a third threshold value and to determine a starting point of a phase in the detected seizure based on the third threshold value. According to a specific embodiment of the invention, the time-point extraction module is further configured to apply a zero-crossing function to the other one of the output signals and to count the number of crossings within a predetermined time window. According to another specific embodiment of the invention, the time-point extraction module is configured to compare the count to a fourth threshold value and to determine at least one time point of the detected seizure based on the fourth threshold value.

This enables the length of the whole seizure and the different phases to be determined automatically without requiring a visual inspection each time, thereby providing a standardized method for detecting the starting point and the end point and thereby the length (time period) of the seizure. By counting the number of crossing, preferably the number of the crossings with a hysteresis, in the high frequency band, the starting point and the end point of the seizure may be determined in a relative simple and effective manner. The end point of the tonic phase and thus the starting point of the clonic phase may likewise be determined in a simple and effective manner by using the low frequency band. By using one of the frequency bands with either the other frequency band or the ratio, the time points may be determined in a more accurate manner. Instead of or in addition, one might count the number of crossing, preferably the number of the crossings with a hysteresis, in the high frequency band which could be used to determine one or more of the time points.

According to one embodiment of the invention, a third analysis module is configured to calculate an averaged signal within a predetermined time window, and where a second evaluation module is configured to calculate the slope of the averaged signal during the beginning of the seizure.

Studies have shown that the initialization of a tonic-clonic seizure begins with a gradually increase in power during the tonic phase which may be described by the slope. This parameter along with other calculated parameters might be used in difficult cases to distinguish between an epileptic seizure (e.g., a GTC seizure) and a PNES (psychogenic non-epileptic seizure).

According to one embodiment of the invention, a fourth analysis module is configured to apply Fourier transformation function to the recorded signal, and where a third evaluation module is configured to calculate the median frequency for a predetermined time window based on the transformed signal.

These median frequencies may be used to generate a power density spectrogram for the electromyographic signal.

According to one embodiment of the invention, a fifth analysis module is configured to determine the coherence between two simultaneous oscillatory activities in a first recorded signal and a second recorded signal.

This coherence may be used to describe the dynamics of the energy in electromyographic signals in the clonic phase as well as the energy of each clonic discharge burst. By using a timer, counter, and a peak detector, the amount of energy in the bursts and the number of clonic discharge bursts may be determined, as well as the number of silent periods between the discharge bursts.

According to one embodiment of the invention, the processor unit is configured to receive a control signal from a unit configured to detect a seizure, and where the processor unit is configured to record the sensed signal for a predetermined time period at least after receiving the control signal. According to a specific embodiment of the invention, the time-point extraction module is configured to determine at least the length of the seizure based on the recorded signal.

This allows the system to only record/log data for about four minutes (two minutes prior and two minutes after a seizure is detected). In one embodiment, the system only records/logs data for about two minutes after the seizure is detected. This reduces the amount of data that needs to be recorded and analyzed, thus reducing the energy consumption in the processor unit. By only logging/recording a limited amount of data, the system may be implemented in a small portable device which is powered by batteries and is capable of being fixed to the body of a user.

Studies have shown that there is an inverse relationship between the length of one part of the tonic phase and the length of the clonic phase which may be described by using a linear or non-linear function. This relationship may be used to calculate the length of the entire seizure, in particular in systems which only records/logs data after a seizure has been detected. The length of the tonic phase may be determined based on the length of the clonic phase since the length of the other part of the tonic phase is substantially the same for all seizures, thereby allowing the length of the seizure to be calculated even when the entire seizure period has not been recorded.

As mentioned above the invention also relates to a method of analyzing the dynamics of a seizure, such as a tonic-clonic seizure, characterized in that:
the recorded signal is filtered and analyzed within a first frequency band of 32-512 Hz and a second frequency band of 2-16 Hz, and
the two output signals are evaluated by calculating a ratio between the first output signal and the second output signal.

This provides a method for determining the characteriztics and thus the dynamics of the seizure without requiring a visual inspection each time, since studies have shown that the power characteriztics of the tonic phase and the clonic phase are mainly located in two different frequency bands: a low frequency band and a high frequency band. This method allows the power generated in the tonic phase and in the clonic phase to be extracted using different frequency bands, thus allowing the dynamics of each phase to be analyzed separately or in relation to each other. The power in the different frequency bands may also be used to detect a seizure, e.g., the onset of a seizure. This enables the method to be implemented as a seizure detection algorithm and/or a seizure analyzing algorithm suitable for a small battery powered portable device located on or near a user.

According to one specific embodiment of the invention, the ratio is compared to a first threshold value, and an event signal is generated if the ratio exceeds the first threshold value.

This allows the algorithm to be used as seizure detection algorithm capable of the detecting a seizure, particularly the onset of a seizure, by simply analyzing the ratio between the power generated in the high and low frequency bands. The number of false positives may be further reduced by ensuring that the value of another parameter also exceeds another threshold value. This parameter may be an averaged value of the power in the high frequency band or in the entire frequency range of the sensed signal since GTC seizures are known to have high RMS values. This configuration allows the algorithm not only to detect seizures, but also to analyze the dynamics of a detected seizure.

According to another specific embodiment of the invention, at least one starting point and an end point is determined based on the two output signals, and that each output signal is at least compared to a threshold value for determining the starting point or the end point.

This allows the algorithm to determine the length of the whole seizure as well as the length of the different phases in the seizure in a standardized manner, thereby eliminating the need for a visual analysis of the signal. These time points may then be used to determine the dynamics of the seizure in combination with other parameters calculated or extracted from the sensed signal.

According to one particular use of the invention, the algorithm is very suitably for detecting and/or analyzing the characteristics of seizures having a tonic phase and a clonic phase.

An embodiment of the invention will now be described by way of example only and with reference to the accompanying drawings.

DETAILED DESCRIPTION OF THE INVENTION

In the following text, the figures will be described one by one and the different parts and positions seen in the figures will be numbered with the same numbers in the different figures. Not all parts and positions indicated in a specific figure will necessarily be discussed together with that figure.

Figure 1:
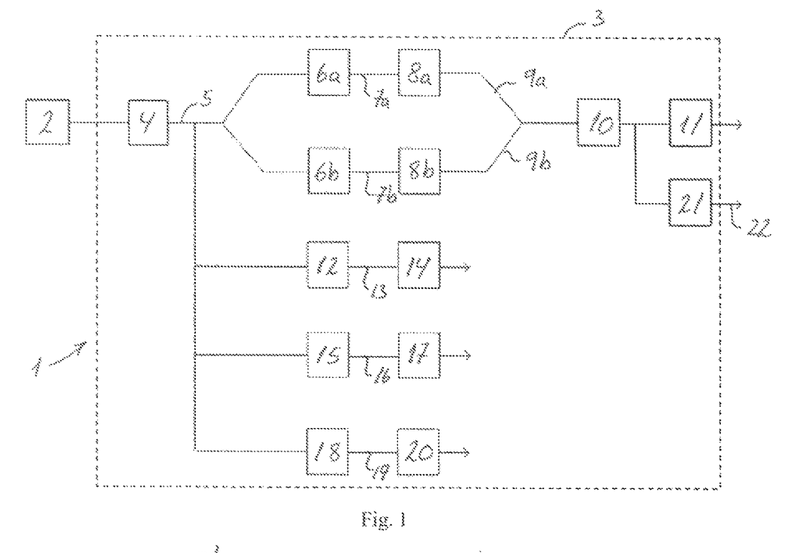
FIG. 1 shows a block diagram of one embodiment of the system according to the invention.

FIG. 1 shows one embodiment of the invention where the system 1 comprises one or more sensor units 2 mounted or fixed to the body of a subject, e.g., a subject suffering from seizures caused by various abnormal neurological activities, such as epilepsy. The sensor unit 2 is configured to measure an electromyographic (EMG) signal generated in the body of the subject. The sensor unit 2 may comprise a number of surface electrodes arranged at strategic positions on the surface of one or more muscles or arranged in or near an outer surface of a sensor housing (not shown) which is configured to lie against the surface of a muscle and to be mounted or fixed to the muscle. The sensor unit 2 is connected to a processor unit 3 and transmits the sensed signal to the processor unit 3 via a wired or wireless connection. The sensor unit 2 may comprise processing means, e.g., filter means, amplifiers and bias circuit for performing an initial processing of the sensed signal before transmittal.

The processor unit 3 is configured to store and analyze the sensed signal from the sensor unit 2 and to determine a number of parameters characterizing the dynamics of the seizure. The processor unit 3 may comprise a sampling module 4 configured to sample, e.g., oversample, the sensed signal at a predetermined sampling frequency. The sampling module 4 may comprise means for filtering out unwanted frequencies and/or biasing the sensed signal, e.g., an anti-aliasing filter. In a preferred embodiment, the sensed signal is filtered using an anti-aliasing filter having a frequency band of 2-512 Hz or alternatively an LP-filter and an HP-filter with said cut-off frequencies.

The sampled signal 5 is then processed using a number of time windows $T_W$ having a predetermined width N. The time windows $T_W$ may be overlapped with a predetermined overlap M. In a preferred embodiment, the sampled signal is processed using at least one time window $T_W$ of 0.2-4 sec. which overlaps the next time window with an overlap M of 10-90%.

Figure 2A:
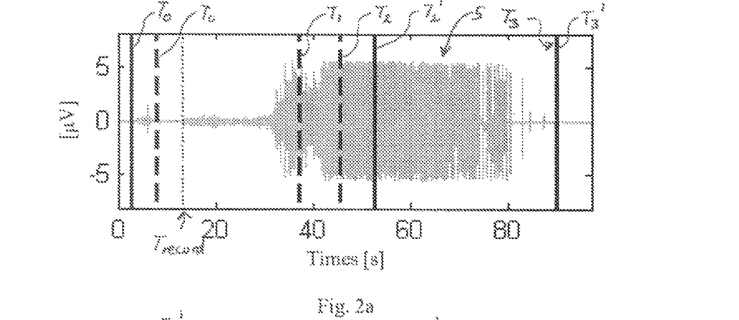
FIG. 2a-b show the sensed signal over the entire frequency range and in a high frequency band and a low frequency band.
Figure 2B:
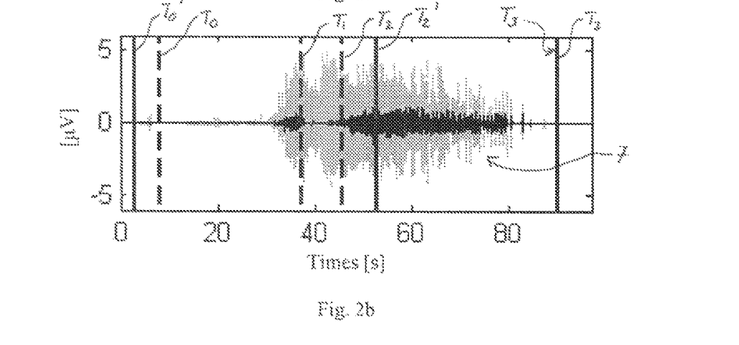

The sampled signal 5, shown in FIG. 2a, is then transmitted to one or more filter modules 6a, 6b configured to filter out the sensed signal within different frequency bands. The bandwidth of each frequency band may be determined according to one or more criteria defining a characterizing pattern for one or more of the phases in the seizure. In one embodiment, a first filter module 6a is configured to filter out the sensed signal within a high frequency band $B_{HF}$ since this band comprises the majority of the characteriztics in power (amplitudes) for a tonic-clonic seizure (an epileptic seizure) compared to the same recorded signal not containing a seizure. A second filter module 6b is configured to filter out the sensed signal within a low frequency band $B_{LF}$ since this band comprises a characterizing pattern for the power (amplitudes) of the tonic phase. In a preferred embodiment, the high frequency band $B_{HF}$ has a frequency band of 32-512 Hz, preferably 64-256 Hz, and the low frequency band $B_{LF}$ has a frequency band of 2-16 Hz, preferably 2-8 Hz. FIG. 2b shows the filtered signal 7 in the high frequency band $B_{HF}$ (black) and in the low frequency band $B_{LF}$ (grey).

Figure 3:
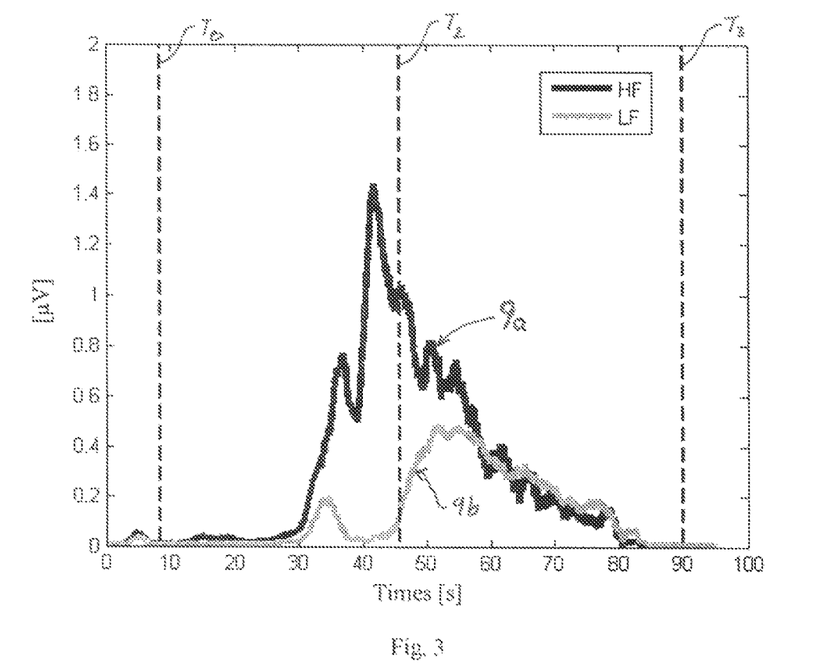
FIG. 3 shows a transformed signal for the high frequency band and the low frequency band.

The filtered signal 7a, 7b is then transmitted to one or more analysis modules 8a, 8b configured to calculate one or more parameters which are later used to determine the dynamics of the seizure. The analysis module 8 is configured to analyze the power (amplitude) of the sensed signal within each frequency band $B_{LF}$, $B_{HF}$. The analysis module 8 uses a wavelet, a Fourier, a chirplet or another suitable transformation function to determine the power content within each frequency band. The analysis module 8 may comprise a rectifying sub-module (not shown) connected to a smoothing sub-module (not shown) configured to generate a transformed output signal 9, as shown in FIG. 3. In a preferred embodiment, the filtered signal 7 is processed using a time window $T_W$ of 2 sec. Each time window may overlap the next time window with 50%. In another preferred embodiment, the filtered signal 7 is processed using a time window $T_W$ of 0.5 sec. Each time window may overlap the next time window with 50%.

Figure 4:
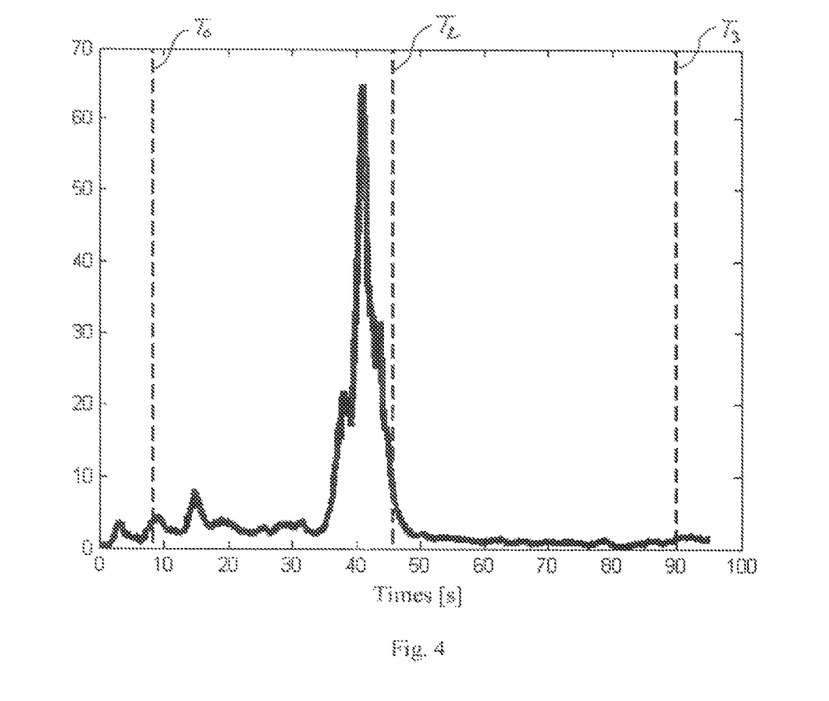
FIG. 4 shows the ratio between the two signals shown in FIG. 3.

The two transformed signals 9a, 9b are then transmitted to an evaluation module 10 configured to calculate the ratio HF/LF between the signals for the two frequency bands $B_{LF}$, $B_{HF}$, as shown in FIG. 4. The evaluation module 10 may be configured to use any known means or functions to compare the value of the high frequency band $B_{HF}$ to the value of the low frequency band $B_{LF}$.

Figure 5:
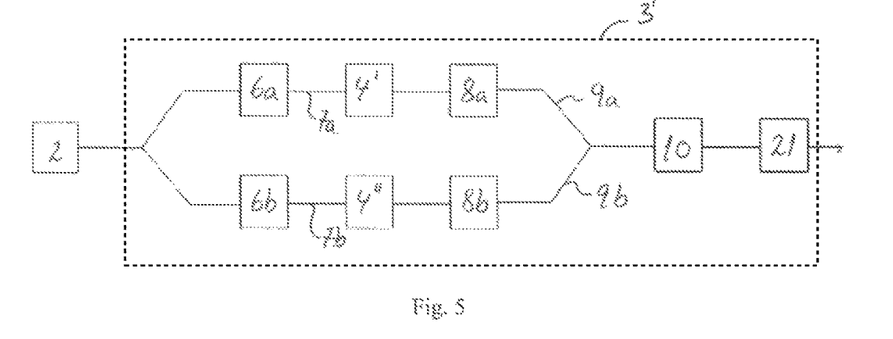
FIG. 5 shows another embodiment of the system according to the invention.

In one embodiment, the sensed signal from the sensor unit 2 is filtered into the different frequency bands before being sampled by sampling module 4, similar to the embodiment shown in FIG. 5. In this embodiment, the filter modules 6a, 6b are connected directly to the sensor unit 2 and are configured to filter the sensed signal into the different frequency bands, such as bands $B_{LF}$ and $B_{HF}$. The filtered signals 7a, 7b are then each transmitted to a sampling module 4', 4" configured to sample, e.g., oversample, the filtered signals 7a, 7b. The sampled signals are then transmitted to the analysis modules 8 which may comprise a rectification sub-module and a smoothing sub-module. The transformed signals 9 are then transmitted to the evaluation module 10. In this embodiment, the sensed signal may also be transmitted to the sampling module 4 so that the entire frequency band B may be analyzed using the other modules 12, 14, 15, 17, 18, 20.

The ratio HF/LF, shown in FIG. 4, is then transmitted to a time-point extraction module 11 configured to at least determine the starting point $T_0$ and end point $T_3$ of the recorded seizure. In one embodiment, the transformed signals 9a, 9b is transmitted to the extraction module 11 instead of or in addition to the ratio HF/LF. The extraction module 11 is configured to compare the transformed signal 9b of the low frequency band $B_{LF}$ to a first threshold value for determining the starting point $T_2$ of the clonic phase. The time point $T_2$ is defined as the time where the transformed signal 9b exceeds the first threshold value after the time point of the peak of the ratio. This time point also defines the end of the tonic phase. The first threshold value may be determined based on the value $P_{record}$ of the ratio HF/LF at the time $T_{record}$ of detecting the seizure. The time point of the maximum value of the ratio HF/LF may be used to determine the time point $T_2$ since the time point of the maximum value of the ratio HF/LF occurs before time point $T_2$.

Figure 6:
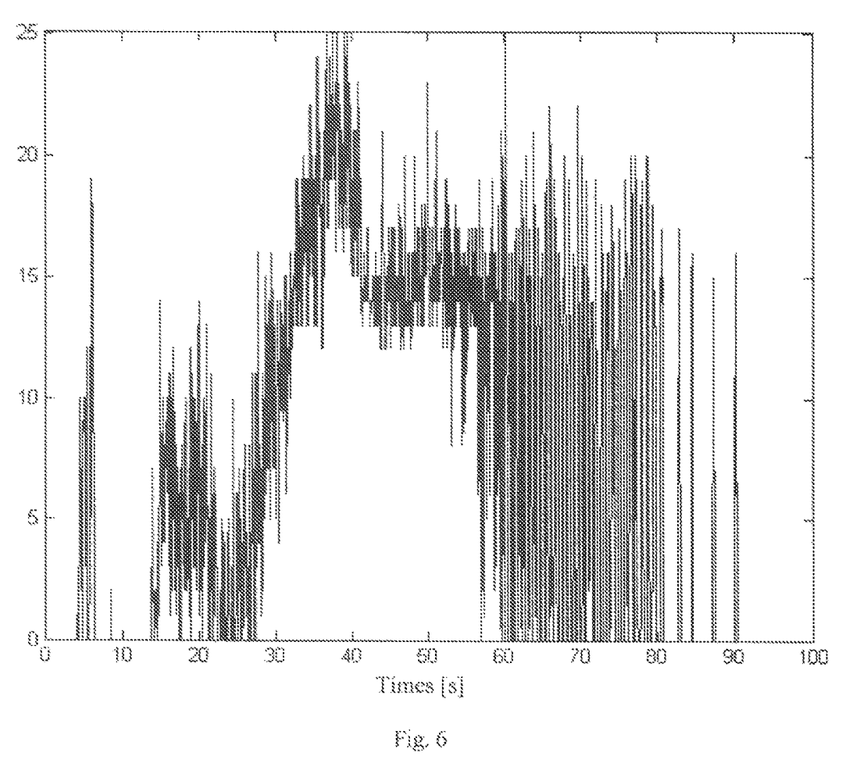
FIG. 6 shows the count of zero-crossings of the high frequency band shown in FIG. 3.

The extraction module 11 is configured to count the number of zero-crossings of the transformed signal 9a of the high frequency band $B_{HF}$ in a predetermined interval (time window), as shown in FIG. 6. In a preferred embodiment, the time window is 20-1024 samples (or about 0.02-1 sec.), preferably 100 samples (or about 0.1 sec.). Each time window may overlap the next time window with 50-90%, preferably 75%. The extraction module 11 may be configured to count the number of crossings with a predetermined hysteresis, e.g., of ±25-75 μV, preferably ±50 μV. The extraction module 11 then compares the counts with a second threshold value for determining the end point $T_3$ of the clonic phase. This time point also defines the end of the seizure. The end point $T_3$ of the clonic phase is in a preferred embodiment defined as the end of the last clonic discharge (CD) burst having a count of 10 or more. The last CD-burst normally occurs within about 90 sec. after the seizure has been detected.

The starting point $T_0$ may be determined by the extraction module 11 by comparing the counts, shown in FIG. 6, to a third threshold value or alternatively the second threshold value used to determine the end point $T_3$. The starting point $T_0$ of the tonic phase may be defined as the start of the first burst having a count of 10 or more. The first burst within the seizure occurs about 30 sec. or less before the seizure is detected.

The processor unit 3 may be configured to limit the recording of data from the sensor unit 1 to about two minutes before and after the detection $T_{record}$ of a seizure according to a first embodiment of the invention in order to record the whole seizure period (length). The processor unit 3 may in a second embodiment be configured to only record data from the sensor unit 2 for about two minutes after the detection $T_{record}$ of a seizure, as described later. The seizure detection may be performed by the processor unit 3 via a seizure detection algorithm implemented in the processor unit 3 or in a second processor unit connected to the processor unit 3.

Based on the determined time points $T_0$, $T_2$ and $T_3$, the extraction module 11 is configured to calculate the length (time period) of the seizure and the different phases respectively. The processor unit 3 may be connected to a central server/unit or external device (not shown) via a wired or wireless connection and may transmit the time points $T_0$, $T_2$, $T_3$ and the lengths to the central server/unit or the external device for further analysis. The corresponding time points $T_0'$, $T_2'$ and $T_3'$ determined by visual inspection are marked with solid lines in FIGS. 2 and 7-9.

Figure 7:
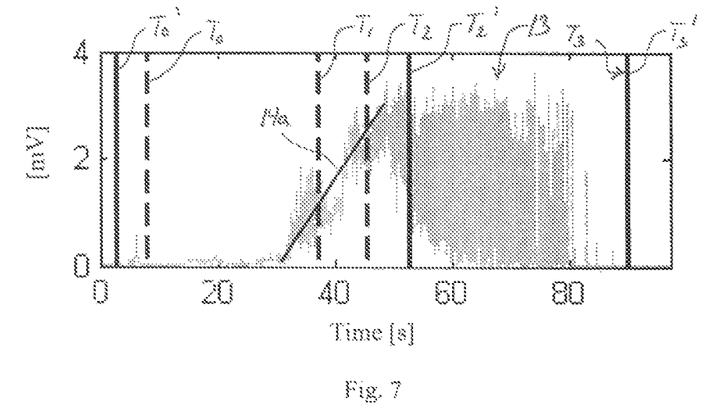
FIG. 7 shows an average signal of the sensed signal over the entire frequency range.

The processor unit 3 may comprise a second analysis module 12 configured to calculate an averaged signal 13, as shown in FIG. 7, for the sensed signal within a predetermined time window. The second analysis module may be configured to apply a root mean square (RMS) function to the sampled signal 5. The second analysis module may alternatively comprise a rectifying sub-module connected to a smoothing sub-module configured to generate the averaged signal 13. In a preferred embodiment, the sensed signal is processed using a time window of 1 sec. Each time window overlaps the next time window by 50%. Alternatively, this module 12 may be omitted and the sampled signal 5 may be transmitted directly to a second evaluation module 14.

The averaged signal 13 is then transmitted to the second evaluation module 14 configured to calculate the slope 14a of the averaged signal during the beginning of the seizure (the tonic phase). The slope 14 is shown in FIG. 7. The second evaluation module 14 determines a time point $T_{begin}$ and a corresponding value for the signal 13 at the beginning of the seizure and a time point $T_{peak}$ and a corresponding value for the signal 13 at the peak of the transmitted signal. The slope 14 is then determined using a linear interpolation between the two reference points. These two time points may differ from the starting point $T_0$ and the time point $T_{record}$. The time point $T_{begin}$ for the beginning may be determined as the time point where the value of the averaged signal 13 starts to increase. In a preferred embodiment, the time point $T_{peak}$ for the peak value is determined as the time point of the maximum value of the ratio HF/LF. The value for the slope 14 may then be transmitted to the central server/unit or the external device.

Figure 8:
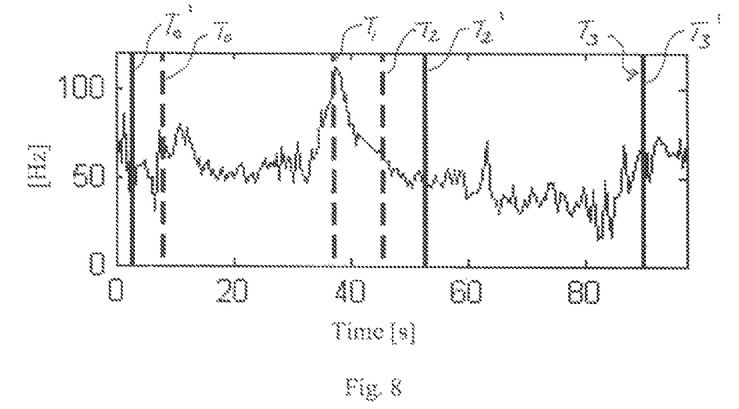
FIG. 8 shows the median frequencies of the sensed signal.

The processor unit 3 may comprise a third analysis module 15 configured to apply a Fourier transformation function to the sensed signal within a predetermined time window (epoch). The transformed signal 16 is then transmitted to a third evaluation module 17 configured to calculate the median frequency for each time window, as shown in FIG. 8. The median frequency is defined as the frequency which divides the magnitude spectrum within each time window into two parts of equal sizes (equal areas under the curve). A smoothing sub-module (not shown) may then be applied to the signal for minimizing segmentation errors. In a preferred embodiment, the sensed signal is processed using a time window of 250 ms. Each time window overlaps the next time window by 50%. The median frequencies may then be transmitted to the central server/unit or the external device.

Figure 9:
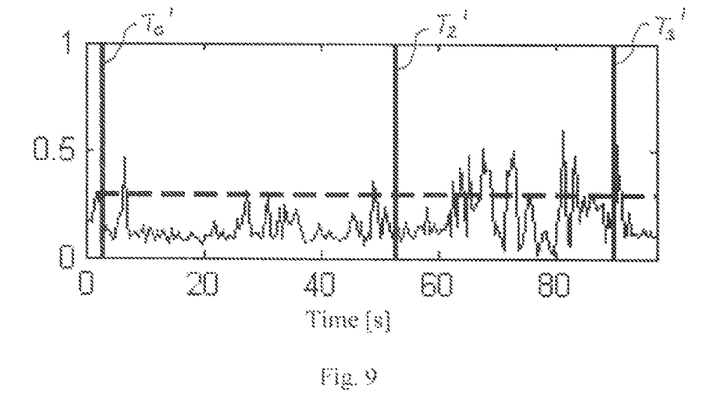
FIG. 9 shows the mean coherence of the sensed signal.

The processor unit 3 may comprise a fourth analysis module 18 configured to determine the coherence between two simultaneous oscillatory activities (a measure for the correlation in the frequency domain). The coherence may be determined based on a first recorded signal, e.g., from a right side muscle, and a second recorded signal, e.g., from a left side muscle. The fourth analysis module 18 may be configured to determine the coherence between a selected activity and an adjacent activity on the left side and on the right side respectively (see, Conradsen et al., supra, which is incorporated by reference). A mean coherence may then be calculated for a predetermined time window, as shown in FIG. 9, using an averaging sub-module (not shown). In a preferred embodiment, the sensed signal is processed using a time window of 1 sec. Each time window overlaps the next time window with 50%.

The value for the coherence 19 may be transmitted to an energy calculation module 20 configured to calculate the energy of the seizure and/or the dynamics of the energy of the seizure. The calculation module 20 may comprise timers, counters and peak detectors which are configured to detect the peak values, the durations (lengths) and the number of the bursts in the seizure, e.g., in the clonic phase. These parameters may then be transmitted to the central server/unit or the external device.

In the second embodiment of the invention, the previously described time points $T_0$, $T_2$, $T_3$ and lengths of the different phases in the seizure may be determined based on data recorded after a seizure has been detected (marked by dotted lines in FIG. 2a). The system may in this embodiment be configured to record data from the sensor unit 2 for about two minutes after a seizure has been detected.

In this embodiment, data from the sensor unit 2 is not recorded by the processor unit 3 until after a seizure has been detected $T_{record}$ by a seizure detection algorithm. This means that data for the entire seizure period is not recorded, leaving parts of the tonic phase unrecorded.

Studies have shown that the length of part of the tonic phase is constant or substantially constant during the detected GTC seizures. These studies have also indicated an inverse-proportional relationship between the length of the other part of the tonic phase and the length of the clonic phase. According to the studies, a short tonic phase was followed by a long clonic phase and vise-versa.

In a simple embodiment, this relationship may be described using a linear function (model) which may be implemented in the extraction module 11, thereby allowing the length of the tonic phase to be based on the length of the clonic phase, or vise-versa. The time point $T_0$ or $T_3$ may be determined using the constant period $T_1$-$T_2$ and the relationship between time periods (lengths) $T_0$-$T_1$ and $T_2$-$T_3$. Time point $T_1$ defines an intermediate time point in the tonic phase used in the subsequent calculations. The extraction module 11 is then able to calculate the length of each phase and thus the length of the seizure based on the recorded data. Other non-linear functions may be used to describe the relationship between time periods $T_0$-$T_1$ and $T_2$-$T_3$. This relationship may also be used to calculate the time points $T_0$ and/or $T_3$ even if the whole seizure period has been recorded, as described in the first embodiment of the invention.

In a third embodiment of the invention, a seizure detection algorithm (not shown) may be configured to detect a seizure, e.g., the onset of a seizure, based on the calculated ratio HF/LF. In one embodiment, the seizure detection algorithm is implemented in the processor unit 3 where the ratio HF/LF calculated by the evaluation module 10 is transmitted to a seizure detection module 21, as shown in FIG. 1. The seizure detection module 21 is configured to compare the ratio HF/LF with a fourth threshold value for detecting the seizure, e.g., the onset of the seizure. The seizure detection module 21 then generates an event signal 22, e.g., an alarm signal, if the ratio HF/LF exceeds/crosses the fourth threshold value. The fourth threshold value may be determined based on the value $P_{record}$. The seizure detection module 21 may be configured to further compare at least one of the signals 9, 13, 16, 19, e.g., the transformed signal 9a of the high frequency band $B_{HF}$ or the averaged signal 13, to a fifth threshold before generating the event signal. The transformed signal 9a of the high frequency band $B_{HF}$ may be averaged, e.g., rectified and smoothed, before being transmitted to the seizure detection module 21. If the ratio HF/LF and the other signal, e.g., signal 9a, exceed/are above the fourth and fifth threshold values respectively, then the event signal is generated. The event signal may be transmitted to an alarm unit (not shown), the central server/unit or the external device. The event signal may activate the recording of the signal from the sensor unit 2, as described above.

In another embodiment, the seizure detection algorithm described above may instead be implemented in a seizure detection unit, e.g., a second processor unit 3', as shown in FIG. 5, where the generated event signal 22 may activate the seizure analysis algorithm/unit, shown in FIG. 1. FIG. 5 shows a simplified embodiment of the seizure detection unit where only the filter modules 6, the sampling modules 4', 4" and analysis modules 8 are shown. The sensed signal may be filtered 7a, 7b before or after being sampled 5', 5", as described above. The sampling modules 4', 4" are configured to sample the sensed signal within the frequency bands $B_{LF}$ and $B_{HF}$. The second processor unit 3' may then transmit the event signal 22 generated by the seizure detection module 21 to the processor unit 3. The event signal 22 then activates the seizure analysis algorithm/unit which may comprise all the modules 4-20 or only modules 4 and 11-20. The second processor unit 3' may further transmit one or more of the signals generated by the modules 6, 8 and 10, e.g., the ratio HF/LF and the transformed signal 9a, to the respective modules in the processor unit 3.

The invention is not limited to the embodiments described herein and may be modified or adapted without departing from the scope of the present invention.

What is claimed is:

1. A system for detecting seizures, such as tonic-clonic seizures, and generating an alarm signal in response to a detected seizure, the system comprising:
   a portable electromyography sensor unit including surface electrodes;
   at least one processor unit capable of recording an electromyography signal from said portable electromyography sensor unit, the at least one processor unit including a filter module, a first analysis module, a second analysis module, an evaluation module, and a seizure detection module;
   the filter module configured to select each of a first frequency band and a second frequency band, the bandwidth of the first frequency band selected to collect muscle related signals in the tonic phase of a generalized tonic-clonic seizure, the bandwidth of the second frequency band selected to collect muscle related signals in the clonic phase of a generalized tonic-clonic seizure;
   said first analysis module configured to analyze the recorded electromyography signal within said first frequency band over a range of 32-512 Hz to provide a first output signal, and said second analysis module configured to analyze the recorded electromyography signal within said second frequency band over a range of 2-16 Hz to provide a second output signal;

said evaluation module configured to calculate a ratio (HF/LF) between said first output signal of the first analysis module and said second output signal of the second analysis module; and said seizure detection module configured to compare the ratio (HF/LF) to a first threshold value and to generate an alarm signal if the ratio (HF/LF) exceeds the first threshold value.

2. A system according to claim 1, wherein the seizure detection module is configured to further compare one of the first or second output signals to a second threshold value and to generate the alarm signal if the first or second output signal exceeds the second threshold value.

3. A system for determining the dynamics of seizures, such as tonic-clonic seizures, the system comprising:

a portable electromyography sensor unit including surface electrodes;

at least one processor unit capable of recording an electromyography signal from said portable electromyography sensor unit, the at least one processor unit including a filter module, a first analysis module, a second analysis module, and a time-point extraction module;

the filter module configured to select each of a first frequency band and a second frequency band, the bandwidth of the first frequency band selected to collect muscle related signals in the tonic phase of a generalized tonic-clonic seizure, the bandwidth of the second frequency band selected to collect muscle related signals in the clonic phase of a generalized tonic-clonic seizure;

said first analysis module configured to analyze the recorded electromyography signal within said first frequency band over a range of 32-512 Hz to provide a first output signal, and said second analysis module configured to analyze the recorded electromyography signal within said second frequency band over a range of 2-16 Hz to provide a second output signal;

said time point extraction configured to compare one of the first or the second output signals to a threshold value and to determine a starting point of a seizure event phase in a detected seizure based on the threshold value.

4. A system according to claim 3, wherein the time-point extraction module is further configured to apply a zero-crossing function to the other one of the first or second output signals and to count the number of crossings within a predetermined time window.

5. A system according to claim 4, wherein the time-point extraction module is configured to compare the count to a second threshold value and to determine at least one time point of the detected seizure based on the second threshold value.

6. A system according to claim 1, wherein a third analysis module is configured to calculate an average of the electromyography signal within a second predetermined time window, and where a second evaluation module is configured to calculate the slope of the average of the electromyography signal during the beginning of the seizure.

7. A system according to claim 1, wherein a fourth analysis module is configured to apply a Fourier transformation function to the electromyography signal to provide a transformed electromyography signal, and where a third evaluation module is configured to calculate the median frequency within a third predetermined time window based on the transformed electromyography signal.

8. A system according to claim 1, wherein the processor unit is configured to receive a control signal and where the processor unit is configured to record the signal for a predetermined time period at least after receiving the control signal.

9. A system according to claim 8, wherein the time-point extraction module is configured to determine at least the length of the seizure based on the electromyography signal.

10. A method of analyzing the dynamics of seizures, such as tonic-clonic seizures, comprising:

measuring an electromyography signal using a portable electromyography sensor unit, including surface electrodes;

recording said electromyography signal from said portable electromyography sensor unit using at least one processor unit, the at least one processor unit including a filter module, a first analysis module, a second analysis module, and a time-point extraction module;

wherein the electromyography signal is filtered using said filter module to select each of a first frequency band and a second frequency band, the bandwidth of the first frequency band selected to collect muscle related signals in the tonic phase of a generalized tonic-clonic seizure, the bandwidth of the second frequency band selected to collect muscle related signals in the clonic phase of a generalized tonic-clonic seizure;

analyzing the electromyography signal using said first analysis module and said second analysis module, said first analysis module analyzing the electromyography signal within said first frequency band over a range of 32-512 Hz to provide a first output signal, and said second analysis module analyzing the electromyography signal within said second frequency band over a range of 2-16 Hz to provide a second output signal; and comparing one of the first or the second output signals to a threshold value to determine a starting point of a seizure event phase in a detected seizure based on said threshold value using said time-point extraction module.

* * * * *